United States Patent
Nguyen et al.

(10) Patent No.: US 11,118,422 B2
(45) Date of Patent: Sep. 14, 2021

(54) AUTOMATED SYSTEM HEALTH CHECK AND SYSTEM ADVISOR

(71) Applicant: Schlumberger Technology Corporation, Sugar Land, TX (US)

(72) Inventors: Dinh Quy Nguyen, Sugar Land, TX (US); Carlos Urdaneta, Houston, TX (US); Gang Qu, Katy, TX (US); Rajnarayanan Balsamy, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 112 days.

(21) Appl. No.: 16/553,300

(22) Filed: Aug. 28, 2019

(65) Prior Publication Data

US 2021/0062612 A1    Mar. 4, 2021

(51) Int. Cl.
    *E21B 33/13*     (2006.01)
    *G05D 7/06*      (2006.01)
    *G01N 33/00*     (2006.01)

(52) U.S. Cl.
    CPC .......... *E21B 33/13* (2013.01); *G05D 7/0617* (2013.01); *G01N 33/00* (2013.01)

(58) Field of Classification Search
    None
    See application file for complete search history.

(56) References Cited

U.S. PATENT DOCUMENTS

| | | |
|---|---|---|
| 4,571,993 A | 2/1986 | St. Onge |
| 5,320,425 A | 6/1994 | Stephenson et al. |
| 5,355,951 A | 10/1994 | Allen et al. |
| 5,455,780 A | 10/1995 | Nguyen et al. |
| 6,125,935 A | 10/2000 | Shahin, Jr. |
| 8,505,625 B2 | 8/2013 | Ravi et al. |
| 8,636,063 B2 | 1/2014 | Ravi et al. |
| 2013/0166263 A1* | 6/2013 | Shen ....................... G06F 30/20 703/2 |
| 2014/0309936 A1 | 10/2014 | Abbassian et al. |
| 2015/0315898 A1 | 11/2015 | Marland et al. |
| 2015/0322775 A1 | 11/2015 | Marland et al. |
| 2017/0002622 A1 | 1/2017 | De Bruijn et al. |
| 2017/0364607 A1 | 12/2017 | Kaushik et al. |
| 2018/0073352 A1 | 3/2018 | Potapenko et al. |
| 2018/0142544 A1 | 5/2018 | Kolchanov et al. |
| 2018/0363414 A1 | 12/2018 | Bogaerts et al. |
| 2019/0264517 A1* | 8/2019 | Chong ..................... B01F 7/18 |
| 2020/0270963 A1* | 8/2020 | Stralow ................... E21B 34/02 |

FOREIGN PATENT DOCUMENTS

WO    2018033234 A1    2/2018

* cited by examiner

*Primary Examiner* — Andrew Sue-Ako

(57) ABSTRACT

Systems and methods for monitoring system health of a well cementing operation are disclosed. A well cementing system includes several fluid pathways and holding/mixing containers. A series of sensors monitors the status of the fluid pathways and the holding/mixing containers. There are redundancies in the fluid pathways, and a preferred order in which the fluid pathways are used. Under normal conditions the fluid for the cementing operation is moved from place to place via the most desired pathway. If the sensors detect a fault, the next-most desired fluid pathway is used. If there are no available fluid pathways, an alarm is issued.

19 Claims, 4 Drawing Sheets

AUTOMATED SYSTEM HEALTH CHECK AND SYSTEM ADVISOR

BACKGROUND

Well cementing is the process of placing cement slurry in a well to achieve several objectives including cementing the casing strings and liners, placing cement plugs, and performing remedial cement procedures. There have been some systems developed to assist with this procedure that can check the status of various components, and can operate with system health check components (for valves, sensors, motors, pumps, etc.). However, there are some drawbacks to these systems. For example, they require an operator to manually check the system status within a few days before the actual cementing operation. Also, if there is a hardware device that has malfunctioned, the operator does not know whether the malfunction will prevent the cementing operation or not.

SUMMARY

Embodiments of the present disclosure are directed to a system including a fluid delivery system configured to mix cement and deliver the cement into a well. The fluid delivery system includes a plurality of fluid origins and fluid destinations. The fluid delivery system is configured to move fluids between any one or more of the fluid origins to any one or more of the fluid destinations via one or more fluid pathways. The system also includes a plurality of sensors configured to monitor a status of the fluid origins, fluid destinations, and fluid pathways, and a plurality of actuators configured to divert fluid into a desired fluid pathway between a fluid origin and a fluid destination. The system also includes a control system configured to communicate with the sensors to record a status of the fluid origins, fluid destinations, and fluid pathways, and a system advisor component configured to store data pertaining to the fluid origins, fluid destinations, and fluid pathways. The data for each fluid origin and fluid destination pair includes a most preferred fluid pathway and at least one lesser preferred fluid pathway. The system advisor is configured to assess a status of the most preferred fluid pathway. If the most preferred fluid pathway is available the system advisor is configured to execute fluid delivery via the most preferred fluid pathway using the actuators. If the most preferred fluid pathway is not available the system advisor is configured to assess a status of a lesser preferred fluid pathway using the actuators. If the lesser preferred fluid pathway is available the system advisor is configured to execute fluid delivery via the lesser preferred pathway using the actuators. If there is no fluid pathway available the system advisor is configured to issue an alarm.

Further embodiments of the present disclosure are directed to a method for monitoring a well cementing operation, including providing a plurality of fluid handling systems that are interconnected by a plurality of fluid pathways that operate together to mix and deliver cement to a location in a well, and monitoring the fluid pathways to determine whether or not the fluid pathways are available to transmit fluid from a fluid origin to a fluid destination. The fluid pathways comprise two or more different pathways between the fluid origin and the fluid destination. The method also includes ranking the fluid pathways in an order from most desirable to least desirable. When the well cementing operation is initiated, the method includes checking the availability of at least one of the fluid pathways, and transmitting the fluid from the fluid origin to the fluid destination via a fluid pathway that is available and most desirable.

In other embodiments the present disclosure is directed to a system including a cementing module comprising a plurality of fluid handling components configured to mix and deliver cement in a well. The fluid handling components include at least one fluid origin, one fluid destination, and two or more fluid pathways configured to transmit fluid from the fluid origin to the fluid destination. The system also includes a plurality of sensors configured to monitor an availability status of the fluid pathways, and an actuator configured to selectively divert fluid into a selected fluid pathway. The system also includes a system advisor configured to store a ranked preference order of the fluid pathways from most desired to least desired, and to provide an availability status of the fluid pathways. The system advisor also can cause the actuator to divert the fluid into a fluid pathway that is most desired and available.

DETAILED DESCRIPTION

Figure 1:
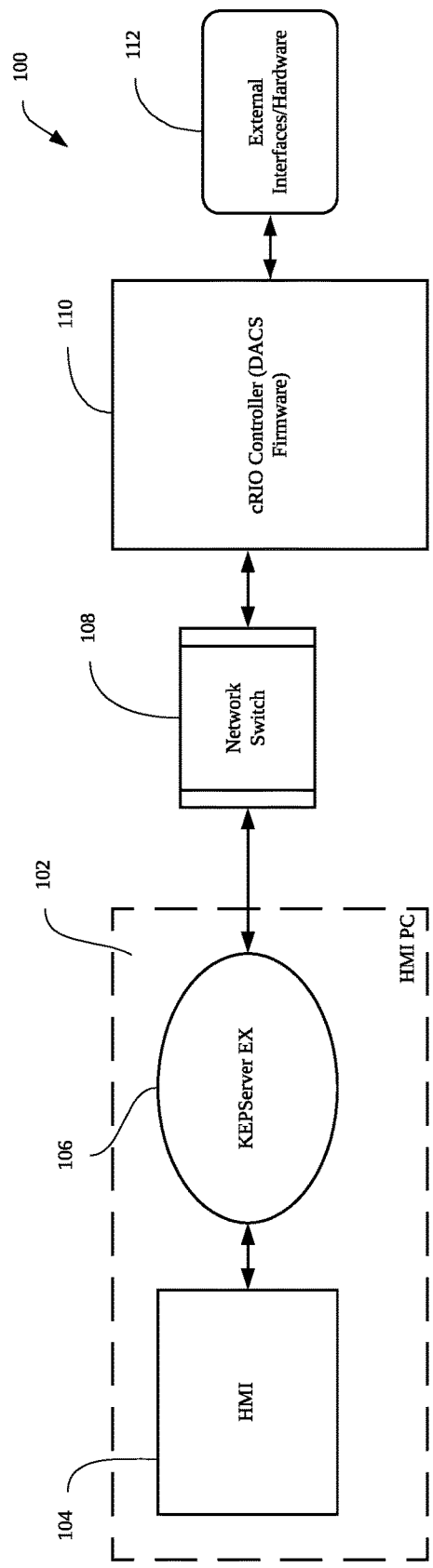
FIG. 1 is a schematic block diagram of an automated system health check and system advisor according to embodiments of the present disclosure.

Below is a detailed description according to various embodiments of the present disclosure. FIG. 1 is a schematic block diagram of an automated system health check and system advisor 100 according to embodiments of the present disclosure. The system 100 includes a HMI PC 102 that itself includes a human machine interface (HMI) 104 and a KEPserver EX 106 that is configured to communicate with a network switch 108. The KEPserver EX 106 is a known component that is commercially available provided by PTC™. Other, similar communication services and components can be used in place of the KEPserver EX 106. The system 100 also includes a cRIO Controller 110 that communicates with the network switch 108 and interfaces with external interfaces/hardware 112. The cRIO controller 110 can be a CompactRIO (or cRIO) that is a real-time embedded industrial controller made by National Instruments™ for industrial control systems. The CompactRIO is a combination of a real-time controller, reconfigurable IO Modules (RIO), FPGA module and an Ethernet expansion chassis. Other, similar components can be used with the system 100 without departing from the spirit of the present disclosure.

Figure 2:
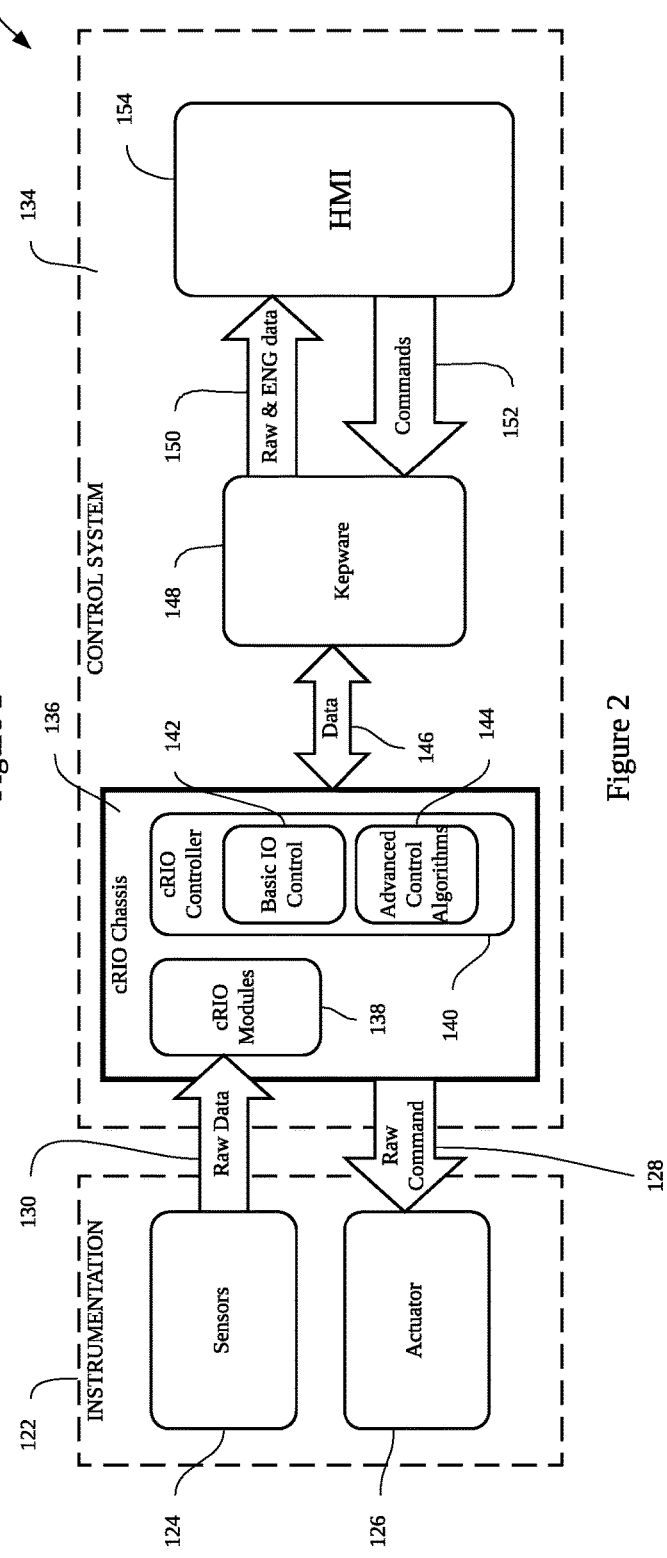
FIG. 2 is a schematic illustration of a system for performing automated system health checks and system advisors according to the present disclosure.

FIG. 2 is a schematic illustration of a system 120 for performing automated system health checks and system advisors according to the present disclosure. The system 120 includes an instrumentation module 122 and a control system 134. The instrumentation module 122 includes sensors 124 and actuators 126 that are configured to communicate with a cRIO module 136 of the control system 134. The sensors 124 provide raw data 130 to the cRIO modules 138 within the cRIO chassis 136. The actuators 126 are configured to receive raw commands 128 from the cRIO chassis 136. The cRIO chassis 136 also includes a cRIO Controller 140 that contains basic 10 control 142 and advanced control algorithms 144. The control system 134 also includes kepware 148 that transmits data 146 to and from the cRIO chassis 136. The control system 134 also includes a HMI 154 that receives raw and engineering data 150 from the kepware 148, and facilitates transmission of commands 152 to the kepware. The commands 152 are eventually passed to the cRIO chassis 136 which then transmits the commands to the actuators 126.

The sensors 124 and actuators 126 can be any of several possible types, such as pressure, temperature, position, chemical composition, accelerometers, or any other suitable type of sensor depending on the equipment that is to be monitored by the sensors. Similarly, the actuators can be any of several possible actuators such as solenoids, valves, pumps, or any other suitable needful type of actuator.

In a cementing operation, there are certain fluids that need to be delivered to different locations within a system. Water and cement are two readily understandable fluids that can be used in a cementing operation, although there may be others. The systems and methods of the present disclosure can be used with any number of fluids and mechanical movements without departing from the scope of the present disclosure. Many of the examples and illustrations herein are given using simplified examples. It is to be appreciated that the systems and methods of the present disclosure can be used equally with different environments and with more diverse fluid compositions.

According to embodiments of the present disclosure, the system 120 can be used to monitor the status of various components of a cementing system. As often as required, the system 120 can check to see if various pipes, pumps, valves, etc. are in an operable condition. The system 120 can therefore maintain a recent status of the components of the system such that when the time comes to initiate a cementing operation it is known that there are no blockages or malfunctioning equipment. Prior art systems would require a manual check of these components some time before the operation begins. The systems and methods of the present disclosure can enable much more up-to-date information about the system which can save time and expense by identifying a problem with the system earlier.

Figure 3:
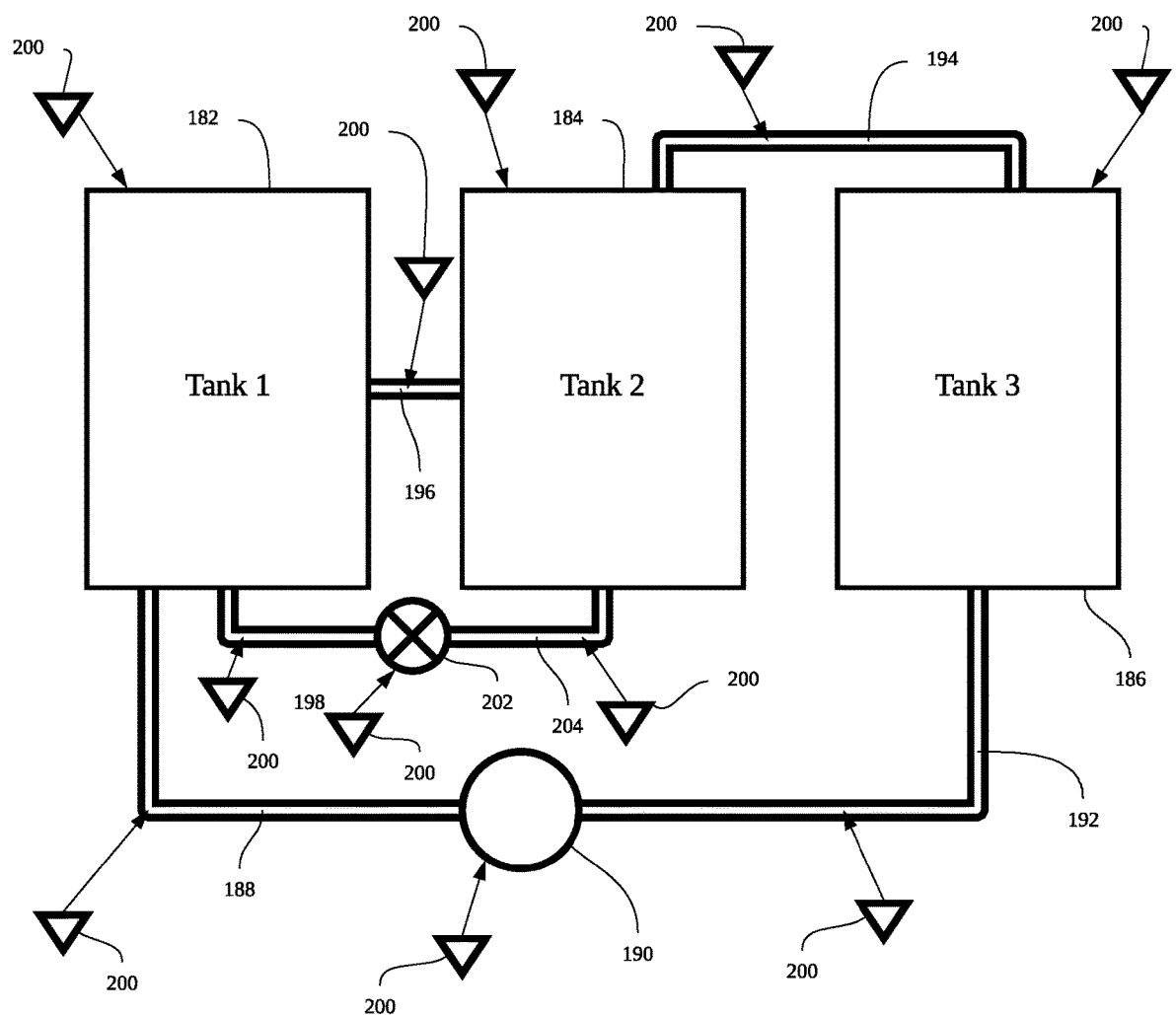
FIG. 3 is a schematic diagram of a system according to embodiments of the present disclosure.

FIG. 3 is a schematic diagram of a system 180 according to embodiments of the present disclosure. The system 180 includes Tank 1 182, Tank 2 184, and Tank 3 186. For purposes of illustration, these three tanks are interconnected via pipes and valves and a cementing operation can require fluid to be moved between any of the Tanks in a certain order. The Tanks can represent holding tanks, mixing tanks, or any other vessel for use with a cementing operation. It is to be appreciated that the system shown is simplified for purposes of explanation and not limitation. In an actual cementing operation there may be many more such components and the system may be more complex. A person of ordinary skill in the art will appreciate that the systems and methods shown and described here are equally applicable to a more complex system.

Tank 1 182 and Tank 2 184 are connected by a pipe 196. There is another route between Tanks 1 and 2, via pipe 198, valve 202, and pipe 204. Tanks 2 and 3 are connected by a pipe 194. Tanks 1 and 3 are connected by a pipe 188, a pump 190, and a pipe 192. Each of these components can have a sensor/actuator 200 coupled thereto. Each instance of the sensor/actuator 200 can be any type of sensor and any type of actuator. In some cases there is a sensor without an actuator and vice versa. The sensor/actuators 200 are coupled to the system 120 shown in FIG. 2.

Suppose for a cementing operation it is needed to store fluid in Tank 1 for a certain period of time, and then to transmit the fluid to Tank 3. There may be a primary path to execute this movement, and the most direct path is usually the most preferred. In this case, the first path is pipe 196 between Tanks 1 and 2 and pipe 194 from Tank 2 to Tank 3. The sensor/actuators 200 can monitor and verify that there is no problem with this path. If there is no problem, the system can execute the transmission directly.

On the other hand, if there is a problem with any of the components in the primary path, the system can search for an alternative path. In the example shown, an alternate path may be to use pipe 188, via pump 190, and pipe 192 that reaches Tank 3. If the sensor/actuators 200 for these components report that there is no problem, the system can execute the transfer via this secondary route. In some embodiments the secondary route is equally capable with the primary route; however, in some cases there is some diminished capacity associated with the secondary route. The diminished capacity can be quantified and this information can be relayed to the system which can make a determination as to the viability of the secondary route. Also, the system may need to make some adjustments to components of the route to accommodate for the diminished capacity. For example, if a pipe segment in a secondary route has a higher pressure drop than the primary segment, a pump upstream of the secondary route can be operated at a higher or lower pressure to accommodate.

The sensor/actuators 200 can be operated by the controllers of the system at any desired rate. In some embodiments the controllers operate at 10 hz, although higher or lower frequencies are possible. This allows an operator to know in virtual real time if there is a problem with the system, and also provides an alternative route if there is a problem. In some cases of course there will be no alternative route, in which case other accommodations must be made. This system provides major advantages over prior art systems in which an operator must arrive at the cementing site sometimes days in advance to manually check the status of the cementing operation and hope that nothing materially changes between the time of the check and the time of the cementing job.

Figure 4:
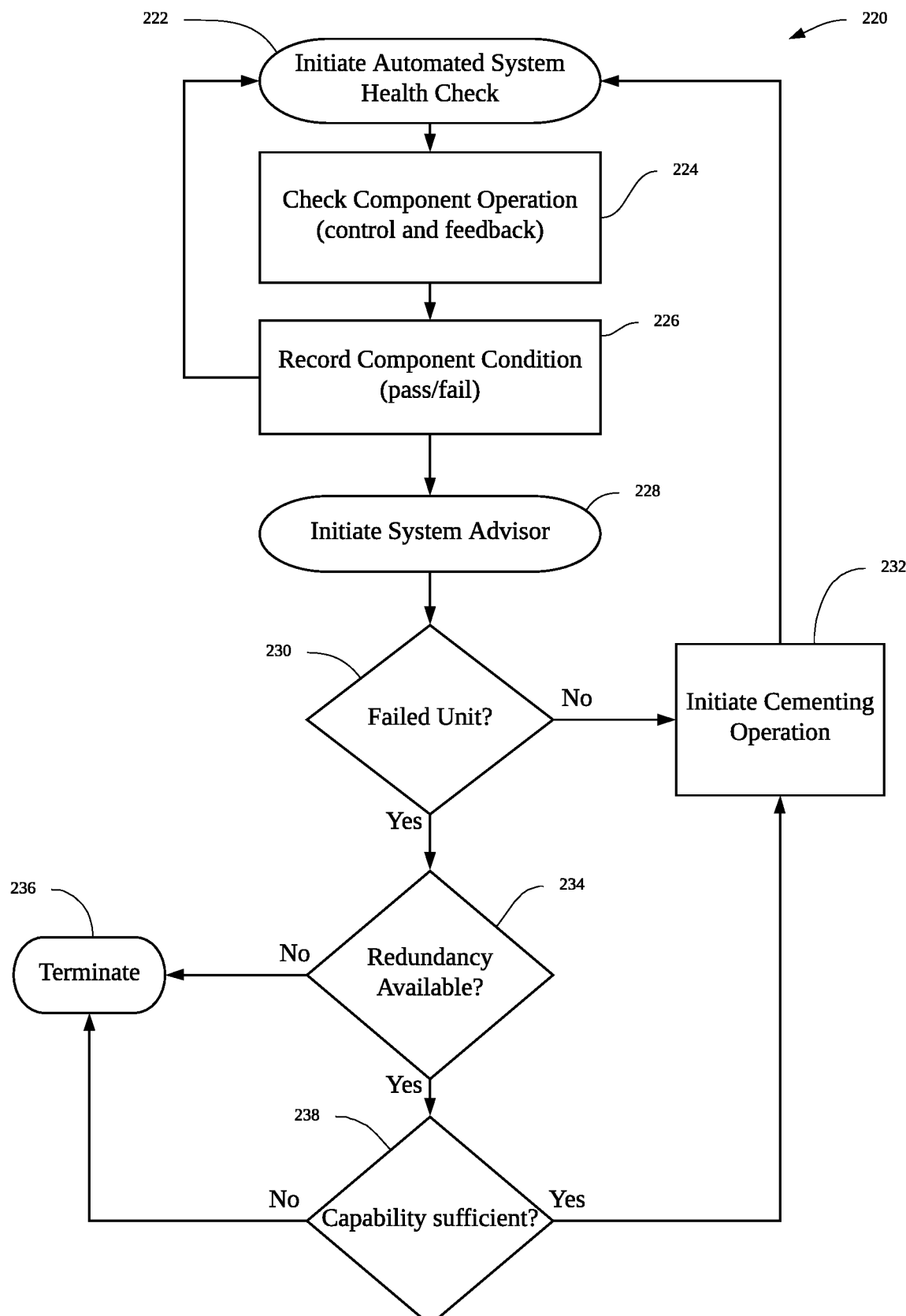
FIG. 4 is a block diagram illustrating operation of methods of the present disclosure.

FIG. 4 is a block diagram 220 illustrating operation of methods of the present disclosure. At 222 an automated system health check is initiated. This can be performed at any time, including long in advance of a cementing operation. At 224 the method includes checking component operation, which can include control and/or feedback. The component to be checked can be any component of the well cementing operation, and can include all major components of the operation. Valves, pipes, pumps, are just a few examples of the components that are checked. At 226 the condition of the components is recorded. The condition can be a simple pass/fail, or it can include more information such as remaining capacity or battery life. This checking and recording represented by 224 and 226 can repeat as often as is practical. In some embodiments a controller operating this system health check can operate on a 10 hz frequency. The status of the components of the cementing operation is therefore known in real time. In some embodiments, if there is a problem an alert can be issued to an operator. In other embodiments, the system simply records the status for a future time at which an operator desires the information.

At 228 a system advisor routine is initiated. This can be an automated event based on the scheduling of the well cementing operation, or it can be initiated by a skilled operator at their discretion. At 230 the method includes checking for any failed units. For each failed component, the remainder of the method 220 can be executed. If there is no failed unit, the cementing operation can be initiated at 232 and the operation carries out without issue. If there is a failed unit, at 234 the system can check for an available redundancy. This represents the secondary path described above. If there are no available alternatives, the system can terminate the operation at 236. If there is an available redundancy, at 238 a check can be performed to identify whether or not the capacity of the secondary route is sufficiently high to carry out the job. Also, the quantity of the diminished capacity can be communicated to allow for adjustments to be made to other components of the cementing operation. Once a satisfactory alternative is identified, the cementing operation can be initiated at 232.

Figure 5:
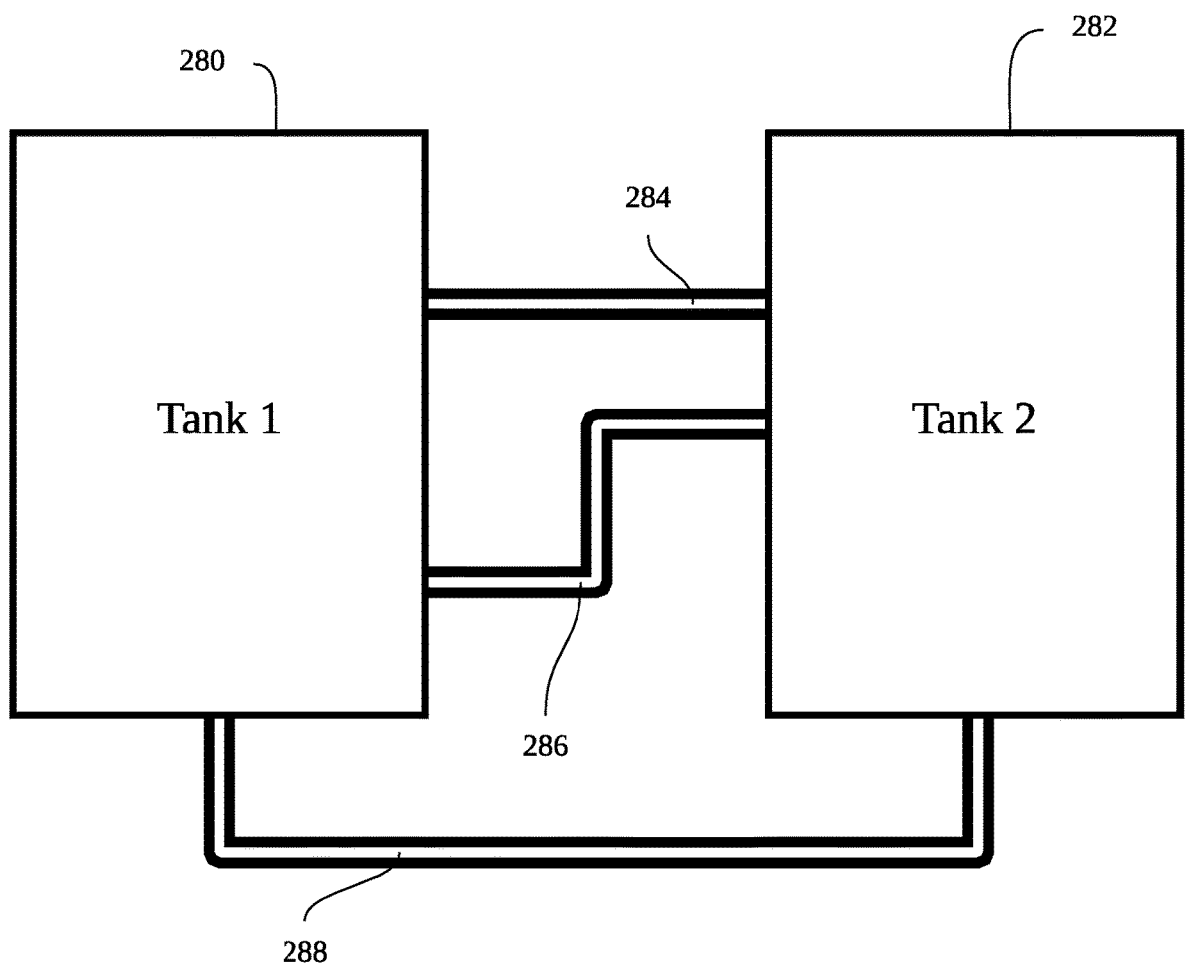
FIG. 5 is an illustration of how alternatives are cataloged according to embodiments of the present disclosure.

FIG. 5 is an illustration of how alternatives are cataloged according to embodiments of the present disclosure. A first tank 280 is connected to a second tank 282 via a primary connection 284. There are two alternative pathways, 286 and 288, each of which achieve the same deliver of fluid from the first tank 280 to the second tank 282. Suppose for example that path 288 involves the use of a valve that can cause a pressure drop and therefore is a less-desirable option. The system can maintain a database with entries for each component that list the available alternatives. For each origin-destination pair, such as the first tank 280 and the second tank 282, there can be a list of pathways, listed in order of preference. When it is time to carry out the cementing operation, the first, most desired pathway can be analyzed. If it is not available, the system can check pathway 286. If it is available, it is used. If not, pathway 288 can be checked. If it is available, it can be used and the diminished capacity of pathway 288 can be communicated to the system to make any necessary adjustments to the cementing operation.

In other embodiments, the system can maintain a list having entries for each pathway component that includes an identifier of the pathway, and a prioritized list of the alternate paths for the pathway. The list for pathway 284 would include pathway 286 and then pathway 288. A list for pathway 286 may include the pathway 288, and may also include a description of the lesser capacity of pathway 288. Pathway 288 may comprise the least-desirable alternative and as such the entry in the database can reflect this and if there is a problem with this pathway then a shut down or other remedy is required.

The foregoing disclosure hereby enables a person of ordinary skill in the art to make and use the disclosed systems without undue experimentation. Certain examples are given to for purposes of explanation and are not given in a limiting manner.

The invention claimed is:

1. A system, comprising:
a fluid delivery system configured to mix cement and deliver the cement into a well, the fluid delivery system comprising a plurality of fluid origins and fluid destinations, wherein the fluid delivery system is configured to move fluids between any one or more of the fluid origins to any one or more of the fluid destinations via two or more fluid pathways;
a plurality of sensors configured to monitor a status of the fluid origins, fluid destinations, and fluid pathways;
a plurality of actuators configured to divert fluid into a desired fluid pathway between a fluid origin and a fluid destination;
a control system configured to communicate with the sensors to record a status of the fluid origins, fluid destinations, and fluid pathways; and
a system advisor component configured to store data pertaining to the fluid origins, fluid destinations, and fluid pathways, wherein the data for each fluid origin and fluid destination pair includes a most preferred fluid pathway and at least one lesser preferred fluid pathway;
wherein:
the system advisor is configured to assess a status of the most preferred fluid pathway;
if the most preferred fluid pathway is available the system advisor is configured to execute fluid delivery via the most preferred fluid pathway using the actuators;
if the most preferred fluid pathway is not available the system advisor is configured to assess a status of a lesser preferred fluid pathway using the actuators;
if the lesser preferred fluid pathway is available the system advisor is configured to execute fluid delivery via the lesser preferred pathway using the actuators; and
if there is no fluid pathway available the system advisor is configured to issue an alarm.

2. The system of claim 1 wherein the data includes a description of a difference in capacity between the most preferred fluid pathway and at least one of the lesser preferred fluid pathways.

3. The system of claim 2 wherein the system advisor is configured to adjust operation of at least one component in the fluid delivery system to accommodate the difference in capacity between the most preferred fluid pathway and the at least one of the lesser preferred fluid pathways.

4. The system of claim 1 wherein the plurality of sensors are configured to monitor the status of the fluid origins, fluid destinations, and fluid pathways at least once per minute.

5. The system of claim 1 wherein the fluid pathways comprise at least one of pipes, valves, pumps, mixing chambers, and holding containers.

6. The system of claim 1 wherein the system advisor is further configured to determine whether a fluid pathway has sufficient capacity to execute the fluid delivery.

7. A method for monitoring a well cementing operation, the method comprising:
providing a plurality of fluid handling systems that are interconnected by a plurality of fluid pathways that operate together to mix and deliver cement to a location in a well;
monitoring the fluid pathways to determine whether the fluid pathways are available to transmit fluid from a fluid origin to a fluid destination, wherein the fluid pathways comprise two or more different pathways between the fluid origin and the fluid destination;
ranking the fluid pathways in an order from most desirable to least desirable;
when the well cementing operation is initiated, checking the availability of at least one of the fluid pathways; and
transmitting the fluid from the fluid origin to the fluid destination via a fluid pathway that is available and most desirable.

8. The method of claim 7 wherein the fluid comprises at least one of water and cement.

9. The method of claim 7 wherein monitoring the fluid pathways to determine whether the fluid pathways are available comprises a "go-no go" analysis.

10. The method of claim 7 wherein monitoring the fluid pathways comprises operating a plurality of sensors at a monitoring frequency of at least 1 hz.

11. The method of claim 7, further comprising storing a capability rating of the plurality of fluid pathways.

12. The method of claim 11, further comprising calculating a difference of capability rating between the most desirable pathway and the fluid pathway that is available and most desirable.

13. The method of claim 7 wherein the fluid pathways comprise at least one of pipes, pumps, valves, and containers.

14. The method of claim 7, further comprising issuing an alarm if there is no available fluid pathway.

15. A system, comprising:
   a cementing module comprising a plurality of fluid handling components configured to mix and deliver cement in a well, wherein the fluid handling components include at least one fluid origin, one fluid destination, and two or more fluid pathways configured to transmit fluid from the fluid origin to the fluid destination;
   a plurality of sensors configured to monitor an availability status of the fluid pathways;
   an actuator configured to selectively divert fluid into a selected fluid pathway; and
   a system advisor configured to:
      store a ranked preference order of the fluid pathways from most desired to least desired;
      provide an availability status of the fluid pathways;
      cause the actuator to divert the fluid into a fluid pathway that is most desired and available.

16. The system of claim 15 wherein the plurality of sensors are configured to monitor availability status of the fluid pathways at a frequency of at least 1 hz.

17. The system of claim 15 wherein the system advisor is further configured to store a capability of the fluid pathways.

18. The system of claim 17 wherein the system advisor is further configured to alter operation of the cementing module according to a difference between the capability of the most desired fluid pathway and the fluid pathway into which the actuator is caused to divert the fluid.

19. The system of claim 15, the system advisor being further configured to issue an alarm if none of the fluid pathways is available.

* * * * *